(12) United States Patent
Zweig et al.

(10) Patent No.: US 6,575,900 B1
(45) Date of Patent: Jun. 10, 2003

(54) METER WITH INTEGRATED DATABASE AND SIMPLIFIED TELEMEDICINE CAPABILITY

(75) Inventors: Stephen E. Zweig, Los Gatos, CA (US); Thomas D. Downey, Cupertino, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/536,881

(22) Filed: Mar. 27, 2000

Related U.S. Application Data

(60) Provisional application No. 60/126,979, filed on Mar. 29, 1999.

(51) Int. Cl.⁷ ............................. A61B 5/00; H04M 11/00
(52) U.S. Cl. ................... 600/300; 600/369; 379/106.2; 128/904
(58) Field of Search ................................. 600/300–301; 128/902–905, 920–925; 705/2–3; 704/2, 3, 5; 345/1, 115, 123; 395/751, 753, 326, 329–332; 379/93.26, 93.33, 106.1–106.2; 370/468

(56) References Cited

U.S. PATENT DOCUMENTS

| | | | |
|---|---|---|---|
| 5,596,994 A | | 1/1997 | Bro |
| 5,905,476 A | * | 5/1999 | McLaughlin et al. .......... 704/2 |
| 5,946,322 A | * | 8/1999 | Moura et al. ............... 370/468 |
| 6,171,237 B1 | * | 1/2001 | Avitall et al. ............... 600/300 |

\* cited by examiner

*Primary Examiner*—Max F. Hindenburg
*Assistant Examiner*—Michael Astorino
(74) *Attorney, Agent, or Firm*—Townsend and Townsend and Crew; William H. May; D. David Hill

(57) ABSTRACT

Medical devices and methods for diagnostic data collection and transmission are described.

20 Claims, No Drawings

METER WITH INTEGRATED DATABASE AND SIMPLIFIED TELEMEDICINE CAPABILITY

This application claims the benefit of the following provisional application under 37 CFR §1.78, 60/126,979, filed Mar. 29, 1999, the full disclosure of which is incorporated herein by reference.

BACKGROUND OF THE INVENTION

The present invention relates to medical methods and devices. More particularly, the present invention relates to diagnostic devices that can be linked to remote data collection and evaluation centers.

Many clinical conditions require monitoring of the status of certain patent metabolic or biochemical parameters. Often, a single reading is insufficient for optimal medical care. Rather, a series of readings over time, combined with other elements of the patient's activities and medical history, are preferable. Readings may be plotted versus time, and trends spotted. Aberrant readings may be understood as being a result of patient non-compliance with a set medical regimen, an unforeseen but understandable change in the patient's metabolic status. Trends and aberrant readings may then be judged on the basis of medication and treatment algorithms appropriate to the patient's condition, and treatment programs appropriately adjusted.

Although some medical conditions, such as elevated cholesterol levels, vary on a long enough time scale so that patients may be appropriately monitored and treated by infrequent visits to medical clinics, other medical conditions, such as diabetes, need for oral anticoagulants, blood pressure or heart conditions, etc. require such a high frequency of monitoring as to make clinic monitoring problematic. For medical conditions where high frequency monitoring is indicated, current trends in medical technology are to provide easy to use, portable, monitoring units (meters) for use in a patient's home environment.

For the above reasons, it is highly useful if the meter has a capability to store data in an on-board meter database, and the ability to recall this stored data whenever the user so desires. Such on-board meter databases have become standard in the diagnostics industry.

Although for an increasing number of analytes, modem technology makes it feasible to perform accurate monitoring in a non-clinical (home) environment, the problem of interpreting the results persists. The algorithms used to adjust patient treatment are often complex, and may require experienced medical judgment. This will obviously not be constantly available in a home environment. Thus methods of conveying data obtained in a non-clinical setting, to a central location where clinical judgment is available, either in the form of preset algorithms, or by on-site clinicians, are of considerable practical interest. Such methods are commonly referred to as telemetry or telemedicine.

A variety of telemedicine methods have been described and practiced. The most common methodologies proposed are schemes for first collecting and storing data using an instrument on-site with the patient. On an occasional basis, telecommunications links are established with clinicians or automated instrumentation at a central, decision making, location, and the stored data is then transferred. At the central location, this data is then processed. Medical opinions may then be relayed to where they are most useful.

Diabetics are one class of patients in need of such capability. For example, as taught by U.S. Pat. No. 4,731,726; diabetic patients may monitor their blood glucose levels with a blood glucose meter that contains an internal database of past readings, and in conjunction with remote communications linkages, work with clinicians to optimally manage their disease. Similarly, U.S. Pat. No. 4,712,562 discloses methods for the remote monitoring of blood pressure.

U.S. Pat. No. 5,704,366 teaches methods for interfacing a patient side system with a remote central database system, using device specific ID codes (essentially a meter serial number) that uniquely identifies a particular remote interface device.

U.S. Pat. No. 5,704,366 teaches methods for rearranging a database of readings, reserved for the meter's internal data storage and recall purposes, in order to facilitate their transmission over a communications link.

U.S. Pat. No. 5,704,366 teaches methods in which the micro-controller on the patient-side meter is coupled to a patient-side telecommunication interface that can transmit analog signals to a remote computer.

U.S. Pat. No. 5,724,580 teaches methods of automatically generating management and prognosis reports and recommending therapy for a patient based on analysis of the downloaded data.

U.S. Pat. No. 3,820,028 teaches digital methods of DTMF decoding.

U.S. Pat. No. 4,484,035 teaches digital methods of DTMF decoding.

U.S. Pat. No. 4,087,638 teaches a DTMF Communication system.

U.S. Pat. No. 5,408,529 teaches a DTMF detector operable in the presence of speech or background noise.

U.S. Pat. No. 5,408,520 teaches conditional methods of switching between a land line telecommunications link, and a cellular communications link, involving the standard AT modem command set, depending upon battery status.

Of the various classes of patients, patients on oral anticoagulants, such as warfarin, have a particular need for a simple, easy to use system that combines accurate diagnostics and telemedicine capability. Such patients may include individuals with deep vein thrombosis, atrial fibrillation, artificial heart valves, myocardial infarction, hematologic disorders such as protein "S" or "C" deficiency, or activated protein C resistance, and many other medical indications. Such patients must maintain their blood coagulation status, monitored by prothrombin time testing, within a narrow therapeutic window. Too little anticoagulation can result in stroke or pulmonary embolism, while too much anticoaguation can result in bleeding or hemorrhage.

Warfarin is a vitamin K antagonist, and is absorbed by the gastrointestinal system to a variable amount depending upon the patient's diet or gastrointestinal status. Patient response to any given dose of warfarin is highly variable between patients. Warfarin's pharmokinetics are such that the effective half-life of the drug is several days. Thus prothrombin-time trend analysis, in conjunction with clinical inquiry as to changes in a patient's diet or general condition, play an important role in managing this drug.

A number of different simple instruments to enable easy assessment of prothrombin time levels in a non-clinical setting have been proposed. For example, U.S. Pat. No. 4,849,340 teaches small disposable cartridge chambers containing dry thromboplastin and magnetic microparticles. The oscillation of the magnetic particles induced by a magnetic field is observed by optical means. Blood is introduced to the chamber, and the length of time required for the thromboplastin mediated blood coagulation to change the optical oscillation signature is proportional to the prothrombin time of the blood sample.

U.S. Pat. No. 5,300,779 teaches a small disposable cartridge chamber containing dry thromboplastin. Blood is introduced to the chamber, and is induced to migrate by capillary action. The movement of blood is observed by laser light scattering techniques. The time elapsed between the time that blood is introduced to the chamber, and the time required for thromboplastin mediated blood coagulation to change the laser light scattering signature, is proportional to the prothrombin time of the blood sample.

U.S. Pat. No. 5,302,348 teaches an alternate type of small disposable cartridge containing capillary tubes and dry thromboplastin. Blood is introduced to the capillary tubes, and the blood induced to move by variations in air pressure. This movement is also observed by optical means. The time elapsed between the application of blood, and the onset of resistance to movement, is proportional to the prothrombin time of the sample.

U.S. Pat. Nos. 5,344,754; 5,418,131; 5,418,143; 5,580,744; incorporated herein by reference, teach a dry reagent "test strip" containing thromboplastin and a fluorescent thrombin substrate reporter molecule. Blood is applied to the test strip. The thromboplastin interacts with the blood sample, producing thrombin, which activates the fluorescent reporter molecule. The time elapsed between the application of blood, and the onset of fluorescence, is proportional to the prothrombin time of the sample.

For these reasons, it is medically useful for patients on oral anticoagulants to have access to simple, easy to use, prothrombin time meters with both on-board databases, and robust, simple, telemedicine capability.

SUMMARY OF THE INVENTION

Although telemedicine capability is obviously highly desirable, many patients in need of such services are frequently elderly and have diminished capability to use sophisticated telecommunications equipment. Telecommunications linkages to such patient's homes may be low-grade telephone lines, often prone to noise and static. It is also difficult for unskilled patients to hook up meters to directly to telecommunications equipment. Frequently, telephone networks employ proprietary digital encoding schemes, that make it difficult to interface by direct electrical means. For such reasons, simplified and robust schemes to enable easy implementation of telemedicine capability under adverse conditions are of high utility.

One method that avoids electrical compatibility issues is direct acoustic linkage, in which a meter is brought in close proximity to a telephone handset. This eliminates the need for any direct electrical linkage between the meter and a telecommunications unit, and additionally gets around problems caused by incompatible equipment. Acoustic coupling has its own set of problems, however, particularly with high-speed modem transmissions. Background noise can distort complex modem acoustic signals. Thus with typical modem technology, mechanical coupler devices to muffle ambient noise, such as the devices taught in U.S. Pat. Nos. 3,619,507 and 4,252,996 are often required in order to get reliable data transmission. Such devices impose a burden on unskilled users, however.

One of the most robust acoustic methods used to communicate small amounts of data is the standard "touch tone" "Dual Tone Multi Frequency" or DTMF methodology. This methodology is able to communicate hexadecimal digits (the numbers 0–9 and letters A–F) by a combination of two audio frequencies. DTMF technology is widely used in the communications industry because its low speed and simple tonal signals allow DTMF signals to be discerned in the highest noise practicable environments.

The standard DTMF frequency matrix is shown in table 1 below:

|        | 1209 Hz | 1336 Hz | 1477 Hz | 1633 Hz |
|--------|---------|---------|---------|---------|
| 697 Hz | 0       | 2       | 3       | A       |
| 770 Hz | 4       | 5       | 6       | B       |
| 852 Hz | 7       | 8       | 9       | C       |
| 941 Hz | */E     | 0       | #/F     | D       |

Because of its extreme robustness and resistance to outside noise, DTMF devices may operate reliably with close, but not perfect acoustic linkage. This is a significant advantage for unskilled users who wish to use a simple meter in conjunction with standard telephone lines, with a minimum of extra equipment or effort. A user may simply bring a meter reasonably close to a broad variety of telephone handsets, and obtain good results with out extra equipment.

Although the methods here can work with the standard DTMF frequencies, it is obvious that alternate frequencies can work as well. In some situations, this may be desirable; to avoid interference with standard DTMF signals. Here DTMF is used in the broadest sense to describe any dual tone multifrequency signaling method, and is not meant to be construed to follow only the specific frequencies as outlined in table 1.

Although DTMF methods are robust, they are extremely slow. A typical DTMF session can transmit about 10 hexadecimal digits a second. Thus, whenever possible, it is preferable to communicate by higher speed linkages, and reserve DTMF as a low speed fallback method.

Thus it is desirable if, before initiating a DTMF session, a meter first automatically checks if a higher speed telecommunications link exists, and if so automatically uses it. One common form of higher speed telecommunications link, suitable for home use, is standard modem technology.

Standard modem technology is well suited for these purposes. In addition to data transmission, it is useful in some situations if a telecommunications link can also provide a voice channel so that numeric readings can be annotated with patient comments. Voice linkage also allows advice from a central location can be relayed to a patient in a timely manner. Fortunately, standard modems have this dual voice/data capability. Typically, commercial modems have a connection to an outside telephone line, a local telephone handset, and a RS232 data line. When the modem is inactive, the local telephone handset is connected to the outside telephone line. When the modem is active, the local handset is disconnected, and the modem takes control of the telephone line.

Typically, modems are controlled by use of a standard "AT" command set. A modem, located either internal or external to the meter, may be queried as to if it is hooked up to a telecommunications link by a set of "AT" commands.

Thus before initiating a fallback DTMF session, it is useful if a meter first checks for the existence of a higher speed modem link using standard modem "AT" commands. If no such higher speed link is found, the meter could then fall back to DTMF use.

Patients also have a need to review and post readings from a meter's database. Typically, meters have user input means, such as a button, which can be activated to allow local viewing of a meter's database. To keep a meter's user interface as simple as possible, in some instances it may be desirable to allow the same user input means used to view a database locally to also engage a meter's automatic search for a high speed telecommunications link. Assuming such search is quick, then the user is not inconvenienced, and the meter interface is kept simple.

Since DTMF fallback is slow and noisy, however, it is usually preferable to have some means of distinguishing a user's desire for local memory playback from the user's desire to establish a telecommunications link. This can be done either by a different user input means, such as a separate button. Alternatively, a single user input means can be used in a distinct mode. For example, a user can hold a button down for a short period of time when local playback is desired, and a longer period of time when a telecommunications link is desired.

In one embodiment of this invention, a meter consists of a local database, and a port for an external modem, so that upon activation of a user recall button, the meter begins a search for an external modem via a set of "AT" commands.

In a second embodiment of this invention, a meter consists of a local database, an internal modem, and a port for an external telephone line. Upon activation of a user recall button, the meter queries the status of the internal modem hook-up to the external telephone line via a set of "AT" commands.

Other embodiments are possible. For example, the meter may incorporate a speaker, or both a speaker and a microphone, and means to either send, or send and receive, acoustic signals such as modem or DTMF signals. Thus a DTMF session could be uni-directional, from meter to remote location only, bi-directional between both the meter and the remote location.

Using modem technology, low cost meter systems may be built around commercially available microcontrollers, such as the Texas Instruments MSP430, that combine on one chip, many discrete functions as Analog/Digital conversion, Liquid Crystal Display drivers, and sufficient processing power to drive digital DTMF encoders and decoders. Such techniques are described in "Generation and Recognition of DTMF signals with the Microcontroller MSP430, Robert Siwy, Texas Instruments Deutschland GmbH report SLAAE16, October 1997," incorporated herein by reference.

In a typical communications session, the user takes the telephone off-hook, and manually or automatically dials into a central database location. The operator at the central location (either human or machine) picks up the line. The meter user then commences a dialog with the central location, in which the meter user receives instructions from the central location, and in turn verbally tells the central location details of the patients medical status, meter status, etc. The central location then prompts the user to press his/her user-input means, such as a memory recall button, upon hearing a carrier tone from the central location. The central location then switches to a modem carrier tone, or a DTMF carrier tone.

Upon hearing the tone, the meter user pushes the memory recall button on the meter. The meter first sends out a series of commands to initialize the meter's modem or DTMF unit. The meter then listens for a proper set of return characters from the central location. If the proper set of return characters is not received within a pre-defined time-out period, the meter instructs the modem/DTMF to turn off (return to on-hook status). The user retains or regains the voice linkage with the central location, and the meter then proceeds to recall previous data on the meter's own internal display. The central location can either elect to discuss the displayed data verbally with the meter user, or alternatively prompt the user to attempt a telemedicine session by resetting the meter, and once again pressing the memory recall button. In either event, a voice linkage with the central location persists until the user chooses to hang up the telephone.

Here the term "button" is used to describe the means used to communicate to the meter that data recall is desired. This may include push buttons, membrane keypads, touch-screen, light pen, and other touch activated sensors.

If a positive data linkage is established with the remote location, the central location then proceeds to download the user identification data from the user data memory, and to determine how many tests have been performed since the last telemedicine session. This can be done by both downloading and examining the status of the user identification and test counter, and comparing this test counter to the number previously stored in a database at the central location. In either event, the central location then calculates how many tests it needs to download, and sends the commands to the meter to retrieve and transmit the appropriate test records. The remote telemedicine session may then optionally choose to update the meter's handshake memory record of the last test number successfully transmitted.

Upon receiving the data, the central location then performs checksum tests to be sure that the data was accurately transmitted, and automatically requests resends of corrupted data as appropriate. The central location can then analyze the data, either automatically, manually, or a combination of the two, for one or more key user performance parameters. These parameters may include:

Proper use of electronic controls or liquid controls

Electronic controls and liquid controls within proper range

Test results within pre-specified clinical limits

Trend analysis on the test results

Test results performed at the desired times and frequencies

Meter clock properly set

Meter modes and calibration properly set

Upon analysis, the central location may then manually, or automatically, advise the user to maintain or change certain practices. For example, advise for more frequent use of controls, more frequent testing, or advise that test results are either outside, or trending to outside, pre-specified clinical limits. The central location may then pass patient results on to a clinician, or alternatively, an on-site clinician may advise as to the next course of action.

For oral anticoagulant treatment, it is particularly advantageous to link voice data with numeric downloaded data as part of the patient record. As an example, oral anticoagulant monitoring is complex and highly individualized. Subtle changes in a patients diet, health status, or activities may perturb results.

Such linkage may be done immediately, as a patient interacts with a live operator at the central location. Alternatively, the patient voice data may be automatically stored by the central location, and reviewed by a human or automated operator at a later time.

Certain modifications to this basic telemedicine process may also be practiced. For example, the meter may contain one or more telephone numbers or access codes within its internal "handshake" memory, and be pre-set to dial into a central location without direct user intervention. The modem or other telemedicine electronics may be built in to the test meter body, or alternatively be external to the meter body, and connected by either a data cable or wireless connection, such as an infra red or radio link.

Example telemedicine session:

Weekly session from a patient assigned to use a prothrombin time meter twice weekly. During this week, the patient ran controls to test meter performance. The patient deviated from his diet, and ate a large salad on Wednesday. The patient has otherwise been compliant with his medication.

Patient hooks meter up to modem unit, and dials a touch-tone telephone to the central location. The central location has caller ID.

Central location: Establishes voice link and confirms patient identity.

Patient: Confirms identity, and explains reason for call.

Central location: Prompts patient to ready meter for data transmission.

Patient: Waits to hear tone, and then presses his meter's "M" button. The meter displays "TEL-on," and establishes a two-way data session with the central location. When this is established, the meter then displays "COM-on."

Central location computer: Sends command to download data from the meter's user data area, containing the patient's ID code. The central computer then reads a number of data records from the meter's data storage memory. Finally, the central computer checks the time and date of the user's meter, and confirms that it is accurate. If it is not, the central computer updates the meter's clock to the correct time and date. The data is then displayed on a computer screen so that a human operator at the central location can then view the recent data. The central location computer then sends a command back to the meter ending the data session, and reestablishing two-way voice communication.

Central location operator: Talks to patient, and reinforces proper use of control testing to ensure good system performance. Questions patient about an aberrant reading.

Patient: Initially unsure why a downloaded reading is aberrant.

Central location operator: Questions patient about possible changes in diet or daily routine.

Patient: After some thought, recalls recent change in diet.

Central location operator: Reviews standing orders from patient's physician. Quotes from the standing order that for this situation, no change in dosage is recommended. Discontinue the changed diet, and repeat testing for three days. If the INR readings are still aberrant, to telephone back with the results within three days. The central location then makes a note of the call and advice in a centralized database, and sets a reminder call for three days in the future.

The above session illustrates the utility of mixed data, voice, and human interactions in managing complex conditions like oral anticoagulant use. Working with an immediate set of hard clinical data on a computer screen, the central operator is then able to interact with the patient, and draw out a hidden fact. That the patient's diet had changed in a way that could interfere with warfarin. Using the hidden fact, and a set of previously authorized medical options, the central operator was able to conclude that a change in the patient's warfarin dosage was not warranted at this time. Without this hidden fact, the operator might have erroneously increased the patient's warfarin dosage.

DESCRIPTION OF THE SPECIFIC EMBODIMENTS

A "test strip" type dry reagent prothrombin time meter, constructed according to the teachings of U.S. Pat. Nos. 5,344,754; 5,418,131; 5,418,143; 5,580,744 and D371,605 was programmed with a 64 record database. Each record of the database consisted of: The test result (INR) number, sample type being analyzed (capillary, venous, plasma), calibration setting of the meter, use or non-use of liquid or electronic control solution, test time and date, number of elapsed tests since the meter was manufactured, user identification code, and a checksum. The meter was programmed so that the input means by which the user could view this database was a "M" button located on the side of the meter. As the user pressed the "M" button down, the meter read through the database, last entry first, and displayed the results to the user as:

RCL 1
ID: 12
MO: 3
DAY 13
YEAR 99
INRc: 1.2
Capb:15

The test counter and checksum values were not displayed, but were available for download.

This let the user know that the last reading, "RCL 1" (recall stored reading number 1) was done by a user (nurse or patient) with identification code 12. The test was done on Mar. 13, 1999. A control solution was done, as can be inferred by the "C" suffix after the INR result. The test result (INR value) was 1.2. The meter was set to read capillary blood, and was using test strips with a calibration code of 15.

Pressing down "M" button caused the meter to retrieve the next to last value, "RCL 2," and so on.

Additionally, the meter was designed to contain a 768-byte user configurable memory. This user data memory was distinct from the 64 record test database. The user data memory was used to facilitate telemedicine sessions, and could contain information such as additional user identification, telephone or access codes and numbers, results from previous telemedicine sessions, etc.

The user configurable memory allowed the meter to be customized with a patient specific ID code, such as the patient's social security number and name. This could be stored and retrieved from the meter's user data memory. By combining the user identification number with the test counter, each test reading downloaded from the meter could be uniquely identified in a larger central database, without the necessity of looking up which meter has been assigned to which patient. Patients could use more than one meter without confusing a central database. This allows a central clinic to set many meters to the same clinic ID code, and then assign each nurse or patient their own unique ID number. Nurses or patients are able to pick a meter at random from a pool of clinic specific meters, enter in their specific ID code, and the central database was able to track which readings came from which nurse or patient at which clinic.

Additionally, the meter had a unique meter identification number. This could be optionally downloaded depending upon the configuration of the remote telecommunications system.

Additionally, the meter had a number of user configuration options, which could be remotely set as a result of the telemedicine session. These user configuration options included: Toggle on/off of obligatory daily quality control testing, Toggle on/off of remote telemedicine seeking activity (as well as the parameters associated with such activity), Toggle on/off & configure printer, and Toggle on/off ability of the local user to change meter modes between capillary blood (the meter's normal use), and venous blood or plasma samples (typically only done in reference laboratories).

The setting of the meter's clock could also be verified remotely, and updated if necessary.

Communications Protocol:

Because embedded microprocessors used for medical meters often are chosen for properties (e.g. good analog/digital conversion, low power consumption, low noise) other than speed, and because programming for embedded processors must be extensively validated, it was advantageous to pick a data transmission scheme that did not require much on-board data processing. To keep this overhead to a minimum, the data transmission scheme used in this example simply made the meters internal database memory available to the remote database location. This pushed the overhead of data manipulation to the more capable and more easily configured remote unit.

As previously discussed, high-speed telecommunications links are the preferred method of communication. Such high speed linkages, which may be through direct electrical link, radio link, optical link, etc. are preferred because the higher speeds are more convenient for the user, and allow for more data to be rapidly communicated. However often users may be in a situation where no such direct high speed telecommunications link exists, but an alternate, low speed acoustic link exists through standard voice telephones, cellular phones, and other acoustic telecommunications methods. In such situations, lower speed acoustic links are still preferable to no link. One such acoustic link method is though the DTMF protocol.

If DTMF fallback is desired, it is important to optimize the communications protocol to accommodate DTMF limitations. The DTMF communications protocol is extremely slow, and can only communicate hexadecimal characters (the numbers 0–9 and letters A–F). Because the meter needs to communicate only a small amount of critical data, in a largely asymmetric manner (e.g., the primary data flow was from the meter to the remote database location). A robust, low speed, asymmetric communications protocol was chosen in which a small number of bytes of data received from the remote location were used to trigger the meter to send a comparatively larger number of bytes in response.

To do this, the meter was programmed to read 8 digit commands of the form: CAAADDXX; where C is the command itself (0,1=ignore); (2,3=read, write meter's memory); (4,5=read, write the meter's Clock); (8=erase meter's memory), (>8 terminate session). AAA is the address of the meter's memory that is the focus of the command. DD is a data byte (for writes) XX is a checksum.

The memory address AAA may be used differently for reads and writes. For meter read commands, reads are understood to mean all data from AA(0-F), and the contents of the least significant memory address command are ignored. By contrast, for meter write commands, all writes directly address the memory byte AAA directly specified in the command.

To ensure fidelity, each command set has an internal checksum XX. In this example, XX is a simple checksum composed of the 2 LSD's of CA+AA+DD=XX (hex addition). If this checksum is valid, the command is processed. Otherwise the meter ignores the command, and responds with an error message. A preset number of errors will result in the termination of the telemedicine session.

Thus the meter write command:

"2A10003A" Will result in the transmission of 16 bytes of meter memory information, starting from memory location A10 and progressing to A1F.

The meter read command:

"3A123480" will result in the meter reading and storing byte "34" into memory location A12.

Example telemedicine session:

A series of readings has been taken, and is stored in the meter's test data memory. The meter was connected to an external modem via a RS232 cable, and the external modem was in turn connected to an external telephone line. The modem was also connected to an external touch-tone telephone.

The user picked up the touch-tone telephone handset, and dialed in to the remote location using the touch-tone keypad. After a voice dialog with the remote location, the remote location then advised the user to press the "M" button when the user hears a carrier signal.

In this configuration, upon pressing a recall button, the meter attempted to initialize an internal or external modem using a standard "AT" command set, using the command:

+++AT&F0&D0&C0A

Upon receipt of this signal, the modem disconnected the touch-tone telephone voice handset from the telephone line, and automatically took over the telephone line for its own data communications use.

The meter then waited a preset time for an appropriate response from the remote database, signaling that the remote database is online.

If the remote database responded, the meter and the remote database exchanged data using the DTMF compatible asymmetric protocol previously discussed.

If the meter received a logoff command from the remote database, or if no response was heard within a preset time-out interval, the meter disconnected the modem using another standard "AT" command set line:

+++ATH

Upon receipt of this signal, the modem automatically reconnected the touch-tone telephone voice handset back to the telephone, allowing the user to regain voice access to the remote database.

What is claimed is:

1. A clinical diagnostic meter comprising:
a microprocessor, time keeping means, and memory means, wherein past test results and times are read and stored in an onboard database adapted to store readings as data entries;
means for linking with a telecommunications system adapted for transmitting data to a remote location; and
user input means for initiating selected meter functions;
whereupon activation of the user-input means, the meter attempts to link to the telecommunications system and wherein the meter performs an automatic search for a higher speed telecommunications link, and if no such link is established, a low speed DTMF acoustic link is automatically initiated.

2. The device of claim 1, in which the meter includes electromagnetic radiation means for linking with the telecommunications system.

3. The device of claim 1, in which the telecommunications system is in direct electrical connection with the meter.

4. The device of claim 3, in which the direct electrical connection is established by an "AT" command set search for an external modem.

5. The device of claim 3, in which the direct electrical connection is by modem signals generated internal to the meter.

6. The device of claim 3, in which the direct electrical connection is a digital serial communications link.

7. The device of claim 1, in which the meter includes acoustic signal means for acoustically linking with the telecommunication system.

8. The device of claim 7, in which the data communications means is by acoustic modem signals.

9. The device of claim 7, in which the data communications means is by acoustic DTMF signals.

10. The device of claim 1, wherein the user input means includes button means for initiating, by a button press, the automatic search for a higher speed telecommunications link.

11. The device of claim 1, in which the onboard database includes user data memory means for the storage and retrieval of user specific identification data.

12. The device of claim 11, in which a database at the remote location identifies and sorts downloaded data using user identification data downloaded from the meter's user specific identification data memory.

13. The device of claim 1, in which the onboard database includes counter means for monitoring how many tests have been successfully performed by the meter.

14. The device of claim 1, in which the meter includes means for measuring blood coagulation.

15. The device of claim 14, in which the meter measures prothrombin time results.

16. The device of claim 1, in which the telecommunications system is adapted to transmit both voice and data in the same session.

17. A clinical diagnostic meter for generating test data relating to medical conditions of a patient, the meter adapted for communication between local and remote locations and for transmitting information representative of such medical conditions to the remote location and receiving commands therefrom, the meter comprising:
  a microprocessor;
  a memory coupled to the microprocessor and adapted to store test data and associated times as data entries;
  a telecommunication linking circuit adapted to link with a telecommunication system adapted to transmit data to and receive commands from the remote location, the linking circuit adapted for operation in a plurality of telecommunications linking modes; and
  a user input adapted to initiate selected meter functions, whereupon activation of the user input, the meter undertakes an automatic search for a higher speed telecommunications link, and upon failure to obtain such higher speed telecommunications link, the meter automatically initiates a DTMF acoustic link mode.

18. The device of claim 17, wherein the user input includes a single switch whereupon activation of the switch, the automatic search for a higher speed telecommunications link is initiated.

19. The device of claim 17, in which meter data sent to the remote location is used for therapeutic oral anticoagulant drug monitoring of patients.

20. A clinical diagnostic meter for generating test data relating to medical conditions of a patent, the meter adapted for communication between local and remote locations and for transmitting information representative of such medical conditions to the remote location and receiving commands therefrom, the meter comprising:
  a microprocessor;
  a memory coupled to the microprocessor and adapted to store test data;
  a telecommunications linking circuit adapted to link with a telecommunication system to transmit data to and receive commands from the remote location wherein the telecommunications linking circuit is adapted to transmit data utilizing an asymmetric communications protocol, such that a command comprising a relatively low number of bytes being sent from a remote location triggers the telecommunications linking circuit to transmit data having a comparatively large number of bytes to the remote station.

* * * * *